(12) United States Patent
Mayer et al.

(10) Patent No.: US 8,093,055 B2
(45) Date of Patent: Jan. 10, 2012

(54) CALIBRATION CARD FOR PHOTOLUMINESCENT OXYGEN SENSORS

(75) Inventors: Daniel W. Mayer, Wyoming, MN (US); Dmitri Boris Papkovsky, County Cork (IE)

(73) Assignees: Mocon, Inc., Minneapolis, MN (US); Luxcel Biosciences, Ltd., Cork (IE)

( * ) Notice: Subject to any disclaimer, the term of this patent is extended or adjusted under 35 U.S.C. 154(b) by 0 days.

(21) Appl. No.: 12/633,110

(22) Filed: Dec. 8, 2009

(65) Prior Publication Data
US 2010/0116017 A1    May 13, 2010

Related U.S. Application Data

(63) Continuation-in-part of application No. PCT/US2009/063037, filed on Nov. 3, 2009.

(60) Provisional application No. 61/112,434, filed on Nov. 7, 2008.

(51) Int. Cl.
*G01D 18/00*    (2006.01)
*G01N 21/76*    (2006.01)
*G01N 1/22*     (2006.01)

(52) U.S. Cl. ............... 436/9; 436/8; 436/127; 436/136; 436/164; 436/166; 436/167; 436/169; 436/172; 436/181; 422/420; 422/82.05; 422/82.08; 422/83; 422/88; 73/1.01; 73/1.02; 73/1.03; 73/1.06; 356/437; 356/440

(58) Field of Classification Search .............. 436/8, 9, 436/127, 136, 138, 164, 166, 167, 169, 172, 436/174, 181; 422/400, 420, 82.05, 82.08, 422/83, 86, 88, 500, 547, 551; 73/1.01, 1.02, 73/1.03, 1.06; 356/436, 437, 440
See application file for complete search history.

(56) References Cited

U.S. PATENT DOCUMENTS
3,612,866 A * 10/1971 Stevens .................. 250/483.1
(Continued)

FOREIGN PATENT DOCUMENTS
WO    2007120637 A2    10/2007

OTHER PUBLICATIONS

Lee, Sang-Kyung et al., "Photoluminescent Oxygen Sensing on a Specific Surface Area Using Phosphorescence Quenching of Pt-Pophyrin", Analitical Sciences, Departament of Bioengineering, Tokyo Institute of Technology, pp. 535-540, Aug. 1997, vol. 13.
(Continued)

*Primary Examiner* — Maureen Wallenhorst
(74) *Attorney, Agent, or Firm* — Sherrill Law Offices, PLLC

(57) ABSTRACT

A calibration tool for use in combination with a photoluminescent oxygen-sensitive working probe and an analytical instrument capable of reading the working probe. The calibration tool is effective for achieving two-point calibration of the analytical instrument, and includes at least first and second solid state compositions having different sensitivities to oxygen. The first composition is an oxygen-sensitive photoluminescent dye that is the same as that in the working probe, embedded within an oxygen-permeable carrier matrix that is the same as that in the working probe. The second composition is an oxygen-sensitive photoluminescent dye that is the same as that in the first composition, embedded within a carrier matrix that is different from that in the first composition. The oxygen sensitivity of the second composition is less than the oxygen sensitivity of the first composition.

27 Claims, 2 Drawing Sheets

U.S. PATENT DOCUMENTS

| | | | |
|---|---|---|---|
| 4,476,870 A | 10/1984 | Peterson et al. | |
| 4,810,655 A | 3/1989 | Khalil et al. | |
| 5,407,829 A | 4/1995 | Wolfbeis et al. | |
| 5,483,819 A * | 1/1996 | Barmore et al. | 73/38 |
| 5,718,842 A | 2/1998 | Papkovsky et al. | |
| 6,153,701 A | 11/2000 | Potnis et al. | |
| 6,330,464 B1 * | 12/2001 | Colvin et al. | 600/316 |
| 6,379,969 B1 | 4/2002 | Mauze et al. | |
| 6,689,438 B2 * | 2/2004 | Kennedy et al. | 428/36.6 |
| 6,777,479 B1 | 8/2004 | Bernard et al. | |
| 7,135,342 B2 * | 11/2006 | Colvin et al. | 436/164 |
| 7,138,270 B2 | 11/2006 | Papkovsky et al. | |
| 7,368,153 B2 | 5/2008 | Barmore et al. | |
| 7,534,615 B2 | 5/2009 | Havens | |
| 7,569,395 B2 | 8/2009 | Havens et al. | |
| 2003/0062262 A1 | 4/2003 | Mansouri et al. | |
| 2006/0002822 A1 | 1/2006 | Papkovsky et al. | |
| 2007/0212789 A1 | 9/2007 | Havens et al. | |
| 2008/0051646 A1 | 2/2008 | Papkovsky et al. | |
| 2008/0117418 A1 | 5/2008 | Claps et al. | |
| 2008/0148817 A1 | 6/2008 | Miller et al. | |
| 2008/0190172 A1 | 8/2008 | Jones | |
| 2008/0199360 A1 | 8/2008 | Shahriari | |
| 2008/0215254 A1 | 9/2008 | Leiner et al. | |
| 2008/0242870 A1 | 10/2008 | Meador et al. | |
| 2009/0028756 A1 | 1/2009 | Shahriari | |
| 2009/0029402 A1 | 1/2009 | Papkovsky | |

OTHER PUBLICATIONS

Eaton, K. et al., "Effect of Humidity on the Response Characteristics of Luminescent PtOEP Thin Film Optical Oxygen Sensors", Sensors & Actuarors B, Elsevier Science B. V., vol. 82, pp. 94-104, 2002.

Technical Manual, "Freudenberg Grafted Products", Sep. 2006, pp. 1-32.

Papkovsky, D. et al., "Phosphorescent Sensor Aproach for Non-Destructive Measurments of Oxygen in Packaged Foods: Optimisation of Disposable Oxygen Sensors and Their Characterization Over a Wide Temperature Range", Departament of Biochemestry National University of Ireland, Analitical Letters, 33 (9), pp. 1755-1777, 2000.

* cited by examiner

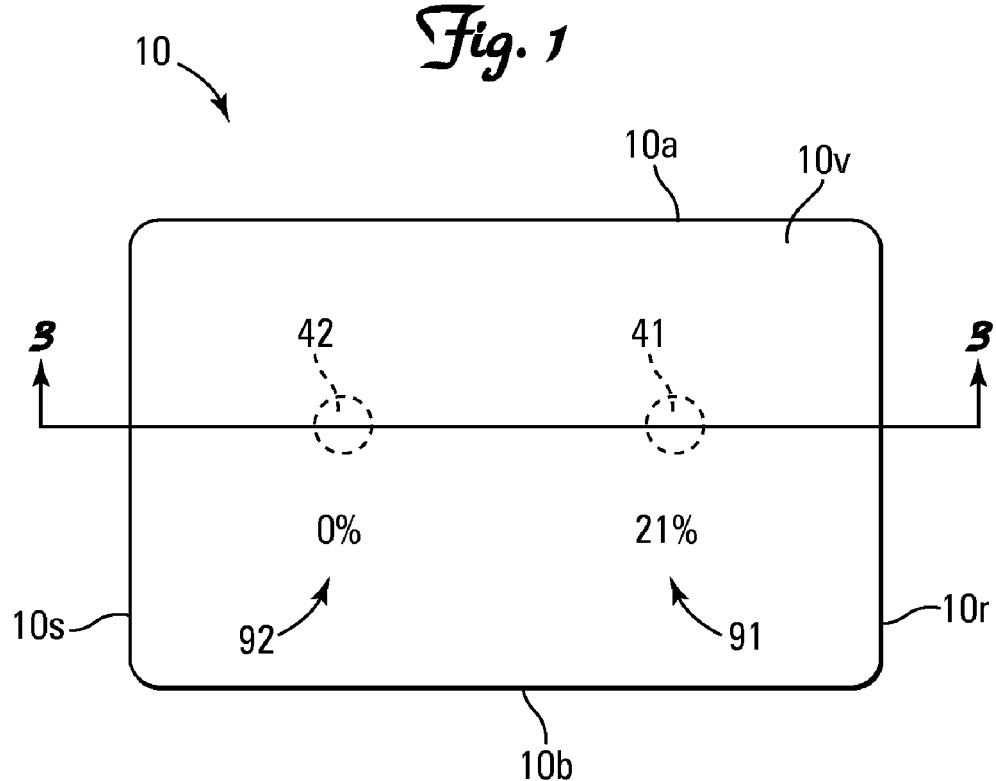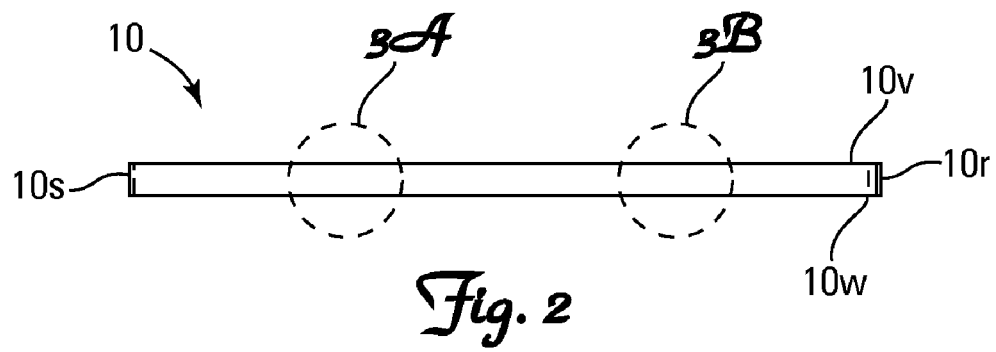

US 8,093,055 B2

CALIBRATION CARD FOR PHOTOLUMINESCENT OXYGEN SENSORS

This application is a continuation-in-part of International Patent Application Serial No. PCT/US2009/063037 filed Nov. 3, 2009, which claims the benefit of U.S. Provisional Application No. 61/112,434, filed Nov. 7, 2008.

BACKGROUND

Photoluminescent sensors or probes are a widely employed method of measuring analyte concentration, typically oxygen, within an enclosed space such as a package or container. Briefly, analyte concentration within a package or container can be measured by placing an analyte sensitive photoluminescent probe within the package or container, allowing the probe to equilibrate within the package or container, exciting the probe with radiant energy, and measuring the extent to which radiant energy emitted by the excited probe is quenched by the presence of the target analyte. Such optical sensors are available from a number of suppliers, including Presens Precision Sensing, GmbH of Regensburg, Germany, Oxysense of Dallas, Tex., United States, and Luxcel Biosciences, Ltd of Cork, Ireland.

Analytical instruments used to read such photoluminescent probes are commonly programmed with a calibration mode that permits calibration of the instrument by having the instrument read probes that have been exposed to mediums having known concentrations of the target analyte (e.g., setting the instrument to calibration mode, reading a probe that has been placed within a container that is flushed with certified tank gas containing 0% analyte, and then reading a probe that has been placed within a container that is flushed with certified tank gas containing a known concentration(s) of analyte such as 100% analyte).

While effective for accurately calibrating optical sensors, this calibration method is time consuming and expensive.

Accordingly, a substantial need exists for a low cost system and method for accurately and reliably calibrating instruments used to read photoluminescent sensors or probes.

SUMMARY OF THE INVENTION

A first aspect of the invention is a calibration card for use in calibrating an analytical instrument capable of reading a photoluminescent oxygen probe from which the concentration of oxygen in a sample communicating with the probe can be determined. The calibration card includes at least (a) a first mass of a first solid state composition comprising an oxygen-sensitive photoluminescent dye that is the same as the probe dye, embedded within an oxygen-permeable carrier matrix that is the same as the probe carrier matrix, wherein the first composition has a first sensitivity to oxygen, and (b) a second mass of a second solid state composition comprising an oxygen-sensitive photoluminescent dye that is the same as the dye in the first mass, embedded within a carrier matrix that is different from the carrier matrix in the first mass, wherein the second composition has a known second sensitivity to oxygen that is less than the first sensitivity to oxygen. The carrier matrix in the second mass is preferably an oxygen impermeable carrier matrix.

A second aspect of the invention is a method of calibrating an analytical instrument capable of reading a photoluminescent oxygen probe from which the concentration of oxygen in a sample communicating with the probe can be determined. The method includes the steps of (a) obtaining a calibration card according to the first aspect of the invention, (b) exposing the first and second masses on the calibration card to a medium having a known concentration of oxygen, (c) setting the analytical instrument to calibration mode, (d) taking a reading from the first mass with the analytical instrument, (e) correlating the value of the reading to the known oxygen concentration to which the calibration card is exposed, (f) taking a reading from the second mass with the analytical instrument, and (g) correlating the value of the reading to an oxygen concentration based upon the known second oxygen sensitivity of the second mass.

A third aspect of the invention is a method of manufacturing a calibration card according to the first aspect of the invention. The method includes the steps of (a) preparing a first coating cocktail which contains the oxygen-sensitive photoluminescent dye of the first mass and the oxygen-permeable carrier matrix of the first mass in an organic solvent, (b) applying the first cocktail to the first major surface of a support material, (c) allowing the applied first cocktail to dry, whereby a solid-state thin film coating of the first mass is formed on the support, (d) preparing a second coating cocktail which contains the oxygen-sensitive photoluminescent dye of the second mass and the oxygen-impermeable carrier matrix of the second mass in an organic solvent, (e) applying the second cocktail to the first major surface of a support material, (f) allowing the applied second cocktail to dry, whereby a solid-state thin film coating of the second mass is formed on the support, and (g) laminating the thin film coatings of the first and second masses to a stiff structural layer at spaced locations on a major surface of the structural layer so as to permit independent readings to be taken from each mass by the analytical instrument.

BRIEF DESCRIPTION OF THE DRAWINGS

FIG. 1 is a top view of one embodiment of the invention.

FIG. 2 is a side view of the invention depicted in FIG. 1.

DETAILED DESCRIPTION OF A PREFERRED EMBODIMENT

Definitions

Figure 3A:
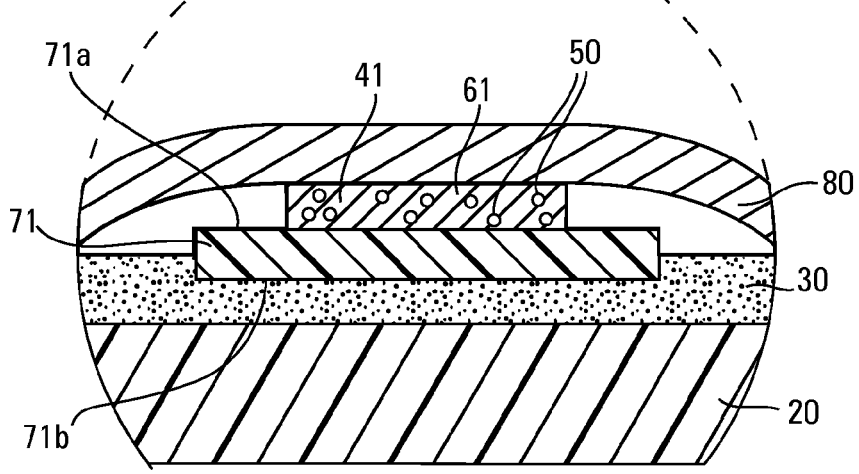
FIG. 3A is an enlarged cross-sectional side view of a portion of the invention shown in FIGS. 1 and 2 taken along line 3-3 and including the 0% oxygen area.

As used herein, including the claims, the phrase "oxygen permeable" means a material that when formed into a 1 mil (25.4 µm) film has an oxygen transmission rate of greater than 1,000 $c^3/m^2$ day when measured in accordance with ASTM D 3985.

As used herein, including the claims, the phrase "highly oxygen permeable" means a material that when formed into a 1 mil (25.4 µm) film has an oxygen transmission rate of greater than 2,000 $c^3/m^2$ day when measured in accordance with ASTM D 3985.

As used herein, including the claims, the phrase "oxygen impermeable" means a material that when formed into a 1 mil (25.4 µm) film has an oxygen transmission rate of less than 100 $c^3/m^2$ day when measured in accordance with ASTM F 1927.

As used herein, including the claims, the phrase "oxygen barrier" means a film, including coated, metalized and multiple layer films, that are impervious to oxygen (such as a layer of metal) or have an oxygen transmission rate of less than 20 c³/m² day when measured in accordance with ASTM F 1927.

As used herein, including the claims, the phrase "oxygen sensitivity" or "sensitivity to oxygen" means sensitivity measured by luminescence quenching.

As used herein, including the claims, the phrase "thin film" means a film having a thickness of less than 10 μm.

Nomenclature
10 Calibration Card
10a Top of Calibration Card
10b Bottom of Calibration Card
10r Right Side of Calibration Card
10s Left Side of Calibration Card
10v Upper Major Surface of Calibration Card
10w Lower Major Surface of Calibration Card
20 Structural Layer
30 Adhesive Layer
40 Masses of Solid State Photoluminescent Compositions
41 First or 21% Mass of Solid State Photoluminescent Composition
42 Second or 0% Mass of Solid State Photoluminescent Composition
50 Oxygen-Sensitive Photoluminescent Dye
60 Carrier Matrixes
61 First Carrier Matrix
62 Second Carrier Matrix
71 First Support Layer
71a Upper Major Surface of First Support Layer
71b Lower Major Surface of First Support Layer
72 Second Support Layer
72a Upper Major Surface of Second Support Layer
72b Lower Major Surface of Second Support Layer
80 Clear Coat or Cover Layer
90 Indicia
91 First Indicia Indicating First or 21% Mass of Solid State Photoluminescent Composition
92 Second Indicia Indicating Second or 0% Mass of Solid State Photoluminescent Composition Construction Referring generally to FIGS. 1 and 2, a first aspect of the invention is a calibration card 10 for use in calibrating an analytical instrument (not shown) for reading photoluminescent sensors or probes (not shown). The calibration card 10 includes first 41 and second 42 masses of an oxygen sensitive photoluminescent composition. The first mass 41 (also referenced as the 21% mass for convenience) comprises an oxygen-sensitive photoluminescent dye 50 that is the same as the oxygen-sensitive photoluminescent dye employed in the probes (not shown) read by the instrument (not shown), embedded within a first carrier matrix 61 that is the same as the carrier matrix employed in the probes (not shown) read by the instrument (not shown). The first mass 41 will have an established, known sensitivity to oxygen. The second mass 42 (also referenced as the 0% mass for convenience), as with the first mass 41, comprises an oxygen-sensitive photoluminescent dye 50 that is the same as the oxygen-sensitive photoluminescent dye employed in the probes (not shown) read by the instrument (not shown), embedded within a second carrier matrix 62. However, the first carrier matrix 61 is selected so as be different from the second carrier matrix 62 so as to render the second mass 42 less sensitive to oxygen than the first mass 41. The first carrier matrix 61 is preferably an oxygen permeable material while the second carrier matrix 62 is preferably an oxygen impermeable material.

Figure 3B:
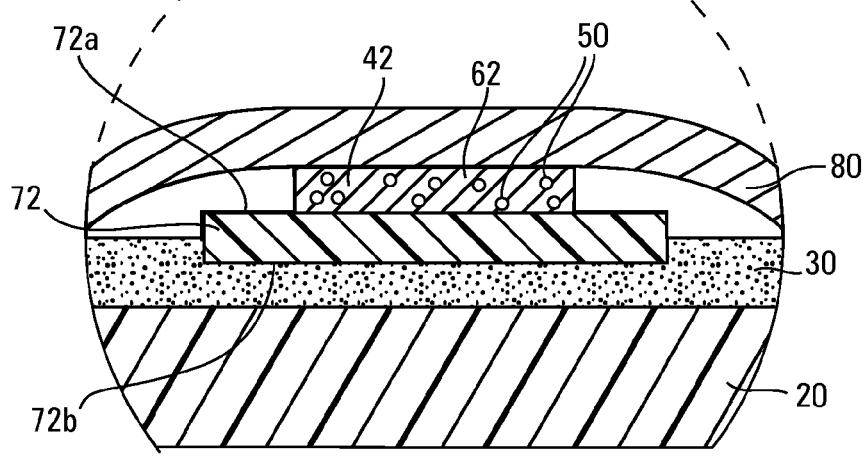
FIG. 3B is an enlarged cross-sectional side view of a portion of the invention shown in FIGS. 1 and 2 taken along line 3-3 and including the 21% oxygen area.

As shown in FIGS. 3A and 3B, the first and second masses of oxygen sensitive photoluminescent composition 41 and 42 (collectively referenced as photoluminescent masses 40) are preferably sandwiched between a structural layer 20 and a cover layer 80. One or both of the structural layer 20 and cover layer 80 should be highly permeable to oxygen so that at least the first mass 41 and preferably both masses 41 and 42 are exposed to an ambient concentration of oxygen (i.e., 21% $O_2$). Alternatively, the structural layer 20 and/or cover layer 80 may be selected from materials that are only moderately permeable to oxygen or even impermeable to oxygen by perforating the layer with one or more openings in at least the area that overlays the masses of oxygen sensitive photoluminescent compositions 40. An adhesive layer 30 may be used to secure the cover layer 80 and the photoluminescent masses 40 onto the support layer 20.

The calibration card 10 has a top edge 10a, a bottom edge 10b, a right side edge 10r, a left side edge 10s, an upper major surface 10v and a lower major surface 10w. The card 10 should have a length of about 4 to 20 cm, a width of about 4 to 20 cm, and a thickness of less than 1 cm. A card 10 smaller than this is prone to being lost or misplaced while a card 10 larger than this becomes unnecessarily bulky. The card 10 preferably has a length of about 6 to 10 cm, a width of about 4 to 8 cm, and a thickness of less than 3 mm, and most preferably matches the size of a standard credit card (i.e., about 8.5 cm long, 5.5 cm wide and about 1 mm thick).

The card 10 can be flexible and should be durable and wear resistant.

The structural layer 20 contributes the bulk of the structural integrity to the card 10. The structural layer 20 may be transparent, translucent or opaque as desired. The structural layer 20 is preferably permeable to $O_2$ and most preferably highly permeable to $O_2$, for purposes of ensuring that at least the 21% mass 41 and preferably both the 21% and the 0% masses 41 and 42 are exposed to an ambient concentration of oxygen (i.e., 21% $O_2$). Suitable materials include specifically, but not exclusively, perforated card stock, perforated paperboard and perforated rigid plastic films.

Adhesive layer 30 may be selected from a wide variety of adhesives suitable for use in laminating cellulosic and/or plastic layers together, including various hot melt and pressure-sensitive adhesives. It may also be possible to forgo the use of the adhesive layer when the structural layer 20 and cover layer 80 are capable of being bound directly to one another, such as by heat welding.

The oxygen sensitive photoluminescent masses 40 include an oxygen-sensitive photoluminescent dye 50 embedded within an oxygen-permeable carrier matrix 60.

The same oxygen-sensitive photoluminescent dye 50 is used in both the 21% and the 0% masses 41 and 42, and is selected to match the oxygen-sensitive photoluminescent dye used in the sensors or probes (not shown) that are read by the analytical instrument (not shown) being calibrated. The oxygen-sensitive photoluminescent dye 50 may be selected from any of the well-known oxygen sensitive photoluminescent dyes used in the construction of oxygen sensitive photoluminescent probes (not shown). A nonexhaustive list of such oxygen sensitive photoluminescent dyes 50 includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium(III) or osmium(II).

The oxygen-sensitive photoluminescent dye 50 is compounded with a suitable carrier matrix 60. The carrier matrix 61 employed in the 21% mass 41 is selected to be the same as the carrier matrix employed in the probes (not shown) read by the instrument (not shown) to be calibrated. Compositions used as the carrier matrix in oxygen-sensitive probes (not shown) are oxygen-permeable compositions, preferably highly oxygen permeable compositions. One of routine skill in the art is capable of selecting such oxygen-permeable carrier compositions 61. A nonexhaustive list of polymers suitable for use as the carrier matrix 61 in the 21% mass 41 includes specifically, but not exclusively, silicone, polystryrene, polycarbonate, polysulfone, and some other polymers and co-polymers. The first mass 41 on the calibration card 10 is preferably produced by the same process as the probes (not shown) that are intended to be read by the instrument (not shown) to be calibrated with the calibration card 10. Most preferably, the first mass 41 and the probes (not shown) that are intended to be read by the instrument (not shown) are produced in the same run from the same batch of photoluminescent composition.

In contrast, the carrier matrix 62 employed in the 0% mass 42 is selected to be less permeable to oxygen than the carrier matrix 61 employed in the 21% mass 41, and is preferably an oxygen-impermeable composition that renders the 0% mass 42 at least 10 times less sensitive to oxygen than the 21% mass 41, more preferably at least 50 times less sensitive to oxygen than the 21% mass 41, and most preferably at least 100 times less sensitive to oxygen than the 21% mass 41.

The 0% mass 42 preferrably generates a photoluminescence intensity signal that is no more than about a degree of magnitude higher or lower than the photoluminescence intensity signal of the probes (not shown) read by the instrument (not shown) being calibrated. A 0% mass 42 that generates a photoluminescence intensity signal that is more than a degree of magnituse higher or lower than the photoluminescence intensity signal of the probes (not shown) read by the instrument (not shown) can lead to increased calibration error. One of routine skill in the art is capable of selecting a suitable carrier matrix 62. A nonexhaustive list of suitable polymers for use as the oxygen-impermeable carrier matrix 62 includes specifically, but not exclusively, polyvinylidine chloride copolymers such as polyvinylidine chloride—polyvinyl chloride and polyvinylidene chloride-acrylonitrile, polyvinyl chloride, polyvinyl alcohol, polyethylene vinyl alcohol and polymethylmethacrylate.

Typically, the oxygen sensitive photoluminescent masses 41 and 42 are coated onto the first major surface 71a, 72a of a support layer 71, 72 respectively (collectively 70). The support layers 71 and 72 are sheets or films having first and second major surfaces 71a, 71b and 72a, 72b respectively, formed from a material that is compatible with the oxygen sensitive photoluminescent masses 40. The support layers 71 and 72 may be the same or different, and may constitute a single sheet or separate sheets of material. One of routine skill in the art is capable of selecting suitable support layer(s) 70. If the oxygen-sensitive masses 40 are applied directly onto the support layer 70, the latter should be compatible with the application process (e.g., adhesion, compatibility with any solvent(s) used, etc.). The support layer 70 can be an oxygen barrier material, with a preference for use of an oxygen barrier material as the support layer 72 for the 0% mass 42. A nonexhaustive list of materials suitable for use as an oxygen barrier support layer 70 includes specifically, but not exclusively, polyethylene terephthalate, polyvinyl chloride, polyethylene and polypropylene. A preferred oxygen barrier support layer 70 is biaxially oriented polyethylene terephthalate.

The support layer 30 is preferably between about 30 μm and 500 μm thick.

The cover layer 80 provides additional structural integrity to the card 10 and serves as a protective covering for the photoluminescent masses 40. At least those areas of the cover layer 80 that overlay the oxygen-sensitive photoluminescent masses 40 need to be transparent or translucent at least at the specific wavelengths at which the oxygen-sensitive photoluminescent dye 50 absorbs and emits radiation. The cover layer 80 is preferably permeable to $O_2$ and most preferably highly permeable to $O_2$, for purposes of ensuring that at least the 21% mass 41 and preferably both of the masses 40 are exposed to an ambient concentration of oxygen (i.e., 21% $O_2$). Suitable materials include specifically, but not exclusively, plastic films of polyethylene, polypropylene, polystyrene, and preferably perforated films (e.g., perforated films of polyvinylchloride or polyester) which provide fast gas exchange. Alternatively, the cover layer 80 may be selected from materials that are only moderately permeable to oxygen or even impermeable to oxygen by perforating the layer 80 with one or more openings in at least the area that overlays the masses of oxygen sensitive photoluminescent compositions 40.

The upper major surface 10v of the card 10 is imprinted with first indicia 91 and second indicia 92 (collectively indicia 90) for identifying the first photoluminescent mass 41 as the mass representative of a probe (not shown) exposed to an environmental concentration of oxygen (e.g., 21%, Twenty One, High, Maximum, Atmosphere, etc.), and identifying the second photoluminescent mass 42 as the mass representative of a probe (not shown) exposed to limited oxygen (e.g., 0%, Zero, Low, Minimum, etc.).

Manufacture

The calibration card 10 can essentially be manufactured by the traditional methods employed for manufacturing oxygen-sensitive photoluminescent probes (not shown). Briefly, the card 10 can be conveniently manufactured by (A) preparing a first coating cocktail (not shown) which contains the oxygen-sensitive photoluminescent dye 50, such as Pt-octaethylporphine-ketone, and the oxygen-permeable carrier matrix 61 of the first mass 41, such as polystyrene, in an organic solvent (not shown) such as ethylacetate, (B) applying the first cocktail (not shown) to the first major surface 71a of a support material 71, such as a polyethylene terphthalate or a polypropylene film, (C) allowing the applied first cocktail (not shown) to dry, whereby a solid-state thin film coating of the first mass 41 is formed on the support 71, (D) preparing a second coating cocktail (not shown) which contains the oxygen-sensitive photoluminescent dye 50, such as Pt-octaethylporphine-ketone, and the oxygen-impermeable carrier matrix 62 of the second mass 42, such as polyvinylidene chloride-acrylonitrile co-polymer, in an organic solvent (not shown) such as acetone, (E) applying the second cocktail (not shown) to the first major surface 72a of a support material 72, (F) allowing the applied second cocktail (not shown) to dry, whereby a solid-state thin film coating of the second mass 42 is formed on the support 72, and (G) laminating the thin film coatings of the first and second masses 41 and 42 to a stiff structural layer 20 at spaced locations on an upper major surface 10v of the structural layer 20 so as to provide at least the first mass 41 with access to atmospheric oxygen and permit independent readings to be taken from each mass 41 and 42 by an analytical instrument (not shown).

Generally, the concentration of the carrier matrix 60 in the organic solvent (not shown) should be in the range of 0.1 to 20% w/w, with the ratio of dye 50 to carrier matrix 60 in the range of 1:50 to 1:5,000 w/w.

When employed, the adhesive layer 30 and the cover layer 80 may be coated or laminated to the upper major surface (unnumbered) of the structural layer 20 by any of the well known coating and laminating techniques used by converters.

The first mass 41 on the calibration card 10 is preferably produced by the same process as the probes (not shown) that are intended to be read by the instrument (not shown) to be calibrated with the calibration card 10. Most preferably, the first mass 41 and the probes (not shown) that are intended to be read by the instrument (not shown) are produced in the same run from the same batch of photoluminescent composition.

Use

The calibration card 10 can be used to quickly and easily calibrate an instrument (not shown) used to read photoluminescent oxygen probes (not shown) or plurality of photoluminescent oxygen probes (not shown), provided the instrument (not shown) has a calibration mode and has been preprogrammed with data indicating the oxygen concentrations to be correlated with readings taken from the first and second masses 41 and 42 (e.g., 21% O2 for the first mass 41 and 0.058% for the second mass 42). Calibration of the instrument (not shown) with the calibration card 10, involves the steps of (1) exposing the first and second masses 40 on the calibration card 10 to ambient air (i.e., a 21% concentration of oxygen), (2) setting the instrument (not shown) to calibration mode, (3) taking a reading from the 21% mass 41 with the analytical instrument (not shown), (4) correlating the value of the reading to the known oxygen concentration to which the calibration card is exposed (e.g., 21%), (5) taking a reading from the 0% mass 42 with the analytical instrument (not shown), and (6) correlating the value of the reading to the preprogrammed oxygen concentration correlated with the 0% mass 42 (e.g., 0.058%).

Correlation of the readings taken by the instrument (not shown) to the masses 41 and 42 on the calibration card 10 can be accomplished in various ways. One technique is to take readings in a predetermined sequence previously input into the instrument (not shown) (i.e., always read the 21% mass 41 first and the 0% mass 42 last). Another technique is to provide the instrument (not shown) with additional data each time a reading is taken effective for indicating which of the masses 41 and 42 was sensed (e.g., a unique bar code provided next to each mass 40 that is read each time a mass 40 is read). Still another technique is to provide the optical oxygen sensor (not shown) with additional data each time a reading is taken effective for indicating the oxygen concentration corresponding to the mass 40 that was read (e.g., user input of 21 after the 21% mass is read and user input of 0 after the 0% mass is read).

Preferably, both the oxygen probes (not shown) and the calibration card 10 operate in photoluminescence lifetime mode. Luminescence lifetime measurements can be performed by any of the known methods, including specifically but not exclusively direct measurement of luminescence decay, measurement of luminescence phase shift, anisotropy, or any other parameter which is related directly or indirectly to the luminescence lifetime of the probe and the first and second masses 41 and 42.

We claim:

1. A calibration tool for use in combination with a photoluminescent oxygen-sensitive working probe and an analytical instrument capable of reading the working probe from which the concentration of oxygen in a sample communicating with the working probe can be determined, wherein the working probe comprises an oxygen-sensitive photoluminescent dye embedded within an oxygen-permeable carrier matrix, the calibration tool effective for achieving two-point calibration of the analytical instrument and comprising:

(a) a first mass of a first solid state composition comprising an oxygen-sensitive photoluminescent dye that is the same as the probe dye, embedded within an oxygen-permeable carrier matrix that is the same as the probe carrier matrix, wherein the first composition has a first sensitivity to oxygen, and (b) a second mass of a second solid state composition comprising an oxygen-sensitive photoluminescent dye that is the same as the dye in the first mass, embedded within a carrier matrix that is different from the carrier matrix in the first mass, wherein the second composition has a known second sensitivity to oxygen that is less than the first sensitivity to oxygen.

2. The calibration tool of claim 1 wherein the carrier matrix in the second mass is an oxygen impermeable carrier matrix.

3. The calibration tool of claim 1 wherein both the first and second masses are in fluid communication with the atmosphere.

4. The calibration tool of claim 3 wherein the matrix component of the second composition is selected from the group consisting of polyvinyl chloride, polymethylmethacrylate, a polyvinylidine chloride—polyvinyl chloride copolymer, a polyvinylidene chloride-acrylonitrile copolymer, and polyethylene vinyl alcohol.

5. The calibration tool of claim 3 wherein the second sensitivity to oxygen is at least 100 times less than the first sensitivity to oxygen.

6. The calibration tool of claim 1 wherein the oxygen-sensitive photoluminescent dye is a transition metal complex.

7. The calibration tool of claim 6 wherein the transition metal complex is selected from the group consisting of a ruthenium bipyridyl, a ruthenium diphenylphenanotroline, a platinum porphyrin, a palladium porphyrin, a phosphorescent complex of a tetrabenzoporphyrin, a chlorin, a porphyrin-ketone, an aza-porphyrin and a long-decay luminescent complex of iridium(III) or osmium(II).

8. The calibration tool of claim 1 wherein the matrix component of the first composition is highly oxygen permeable.

9. The calibration tool of claim 1 wherein the matrix component of the first composition is selected from the group consisting of silicone, polystryrene, polycarbonate, and polysulfone.

10. The calibration tool of claim 1 wherein the second sensitivity to oxygen is at least 10 times less than the first sensitivity to oxygen.

11. A method of calibrating an analytical instrument having a calibration mode that is capable of reading a photoluminescent probe from which the concentration of oxygen in a sample communicating with the probe can be determined, comprising the steps of:

(a) obtaining a calibration tool according to claim 10,
   (b) exposing the first and second masses on the calibration tool to the atmosphere having a known oxygen concentration,
   (c) setting the analytical instrument to calibration mode,
   (d) taking a reading from the first mass with the analytical instrument,
   (e) correlating the value of the reading to the known oxygen concentration of the atmosphere,
   (f) taking a reading from the second mass with the analytical instrument, and
   (g) correlating the value of the reading to an oxygen concentration based upon the known second oxygen sensitivity of the second mass.

12. The method of claim 11 further comprising the step of providing the analytical instrument with data indicating which of the masses on the calibration tool was read first.

13. The method of claim 11 wherein readings and correlations are based upon photoluminescence lifetime.

14. The calibration tool of claim 1, wherein the tool has a length of about 4 to 20 cm, a width of about 4 to 20 cm, and a thickness of less than 1 cm.

15. The calibration tool of claim 5, wherein the tool has a length of about 6 to 10 cm, a width of about 4 to 8 cm, and a thickness of less than 3 mm.

16. The calibration tool of claim 1 wherein at least the second mass is applied as a coating onto an oxygen barrier support layer.

17. The calibration tool of claim 16 wherein the oxygen barrier support layer is selected from the group consisting of polyethylene terephthalate, polyvinyl chloride, polyethylene and polypropylene.

18. The calibration tool of claim 17 wherein the oxygen barrier support layer is biaxially oriented polyethylene terephthalate.

19. The calibration tool of claim 16 wherein the first and second masses are covered by a transparent cover layer.

20. The calibration tool of claim 19 wherein the transparent cover layer is at least one of a highly oxygen permeable or a perforated film.

21. The calibration tool of claim 1 wherein each of the first composition, the second composition and the working probe emit a photoluminescence intensity signal when excited, and the photoluminescence intensity signal from the second composition is within an order of magnitude of the photoluminescence intensity signal of the working probe.

22. The calibration tool of claim 1, wherein the tool contains (i) first indicia tagging the first mass to a calibration value of a probe exposed to an environmental concentration of oxygen, and (ii) second indicia tagging the second mass to a calibration value of a probe exposed to a defined concentration of oxygen that is less than an environmental concentration of oxygen.

23. The calibration tool of claim 22, wherein the first indicia comprises at least a numerical value of 21% and the second indicia comprises at least a numerical value that is less than 1%.

24. The calibration tool of claim 23, wherein the second indicia is 0%.

25. A method of calibrating an analytical instrument having a calibration mode and capable of reading a photoluminescent oxygen probe or plurality of photoluminescent oxygen probes from which the concentration of oxygen in a sample or set of samples communicating with the probe can be determined, comprising the steps of:
(a) obtaining a calibration tool according to claim 1,
(b) exposing the first and second masses on the calibration tool to a medium having a known concentration of oxygen,
(c) setting the analytical instrument to calibration mode,
(d) taking a reading from the first mass with the analytical instrument,
(e) correlating the value of the reading to the known oxygen concentration to which the calibration tool is exposed,
(f) taking a reading from the second mass with the analytical instrument, and
(g) correlating the value of the reading to an oxygen concentration based upon the known second oxygen sensitivity of the second mass.

26. The method of claim 25 wherein the steps of taking a reading from the first and second masses are performed in a predetermined sequence.

27. The method of claim 25 further comprising the step of providing the analytical instrument with data indicating the oxygen concentration of the medium to which the first mass is exposed.

* * * * *